United States Patent [19]

Wreschner

[11] Patent Number: 4,847,165

[45] Date of Patent: Jul. 11, 1989

[54] CARRIER SHEETS OF PAPER AND NITROCELLULOSE BEARING POLYURIDYLIC ACID AND POLYTHYMIDYLIC ACID RESIDUES AND THEIR USE IN THE PREPARATIVE RECOVERY OF MRNA

[76] Inventor: Daniel H. Wreschner, 6, Anna Frank Street, Petach Tikva 49 311, Israel

[21] Appl. No.: 883,686

[22] Filed: Jul. 9, 1986

Related U.S. Application Data

[63] Continuation of Ser. No. 566,162, Dec. 28, 1983, abandoned.

[30] Foreign Application Priority Data

Dec. 28, 1982 [IS] Israel .................................. 67576

[51] Int. Cl.$^4$ ........................ B32B 21/06; C07H 21/02
[52] U.S. Cl. .................................... 428/537.5; 536/29
[58] Field of Search ........................ 536/29; 428/537.5

[56] References Cited

U.S. PATENT DOCUMENTS 4,549,011 10/1985 Herzberg et al. .
4,564,593 1/1986 Tsukamoto et al. ................ 536/27

OTHER PUBLICATIONS

Mevarech et al., J. Biol. Chem., vol. 254, No. 16, pp. 7472–7475 (1979).
C.A. 86 1243u: Varich et al., Use of Poly(u)-Cellulose and Poly(u)—Sepharise for Studying Virus-Specific RNA of New Castle Diease.
C.A. 90 99424j: Egyhazi et al., A Simple Method for Electrophoretic Selection and Fractionation of Poly(A)-containing RNA and Poly(A).

Primary Examiner—Johnnie R. Brown
Assistant Examiner—Jenny Tou
Attorney, Agent, or Firm—Sandler & Greenblum

[57] ABSTRACT

A carried sheet being formed of a cellulose or a nitrocellulose derivative and coated with polyuridylic acid or polythymidylic acid or a mixture thereof. A method of using the carrier sheet for preparative recovery of mRNA.

32 Claims, No Drawings

CARRIER SHEETS OF PAPER AND NITROCELLULOSE BEARING POLYURIDYLIC ACID AND POLYTHYMIDYLIC ACID RESIDUES AND THEIR USE IN THE PREPARATIVE RECOVERY OF MRNA

This is a continuation, of application Ser. No. 566,162 filed Dec. 28, 1983, abandoned.

BACKGROUND OF THE INVENTION

The present invention relates to a method of and means for the recovery of substantially pure messenger ribonucleic acid (hereinafter referred to as mRNA) fraction from a mixture of a plurality of such fractions. Such purification is required for various molecular biological tests, as well as for the purposes of gene therapy and genertic engineering. Hitherto no satisfactory method for the preparative recovery of essentially pure mRNA fractions is known and it is the object of the present invention to provide such a method.

mRNA is a type of ribonucleic acid (RNA) that is present in the biological and cells is recoverable therefrom, amounting to about 2–3% by weight of the total RNA. There are known methods for the separation of the group of mRNA from the remaining RNAs isolated from a particular cell, but problems have been encountered in the preparative resolution of the group of mRNAs into its constituent component.

According to a known method for the separation of the group of mRNA fractions contained in the total RNA recovered from a cell, the total RNA is chromatographed on a column of powderous cellulose or powderous agarose bearing polyuridylic acid (hereinafter "poly-U") or polythymidylic acid (hereinafter "poly-dT") residues. in this manner, the group of mRNA fractions contained in a cell is separated from all the remaining RNAs. The method is based on the reversible binding of mRNA to the poly-U or poly-dT residues via H-bridges.

It is also known to resolve the group of mRNA fractions into its constituent mRNA fractions by means of electrophoresis, using, for example, an agarose or polyacrylamide gel as matrix. Upon the completion of the electrophoresis each constituent mRNA occupies a different zone on the matrix. There have also been reported various transfer techniques by which various biological macromolecules can be transferred to a receiver carrier such as a blotting paper (see for example Southern, (1975) J. Mol. Biol. 98 503–517; Bittner et al. (1980) Analytical Biochemistry 102 459–471; PeFeroen et al. (1982) Febs. Lett. 145 369–372). By all these and other known techniques the mRNA fractions are transferred to a recipient carrier where they are bound by an irreversible covalent bond or a strong pair bond. Consequently, these methods are only suitable for analytical purposes and cannot be used for preparative recovery of mRNA fractions, which are required for such purposes as gene therapy or genetic engineering.

In summary, it is apparent that while electrophoretic resolution of mRNA provides a good analytical method, no simple methods are known for the elution of mRNA fractions from an electrophoresis gel matrix. (See, for example, Rosen et al., (1975) Biochemistry 14, 69–78 at p. 71).

A method for the preparative recovery of individual mRNA fractions has recently been reported by Graeve et al. (1982) Biochemical and Biophysical Researach Communications 107, No. 4 1559–1565. In the introduction on page 1559 the author discusses the prior art as follows:

"Gradient centrifugation did not resolve the complex mRNA fractions very well. The method of choice is gel electrophoresis in polyacrylamide or agarose which results in an excellent resolution especialy when denaturing reagents such as formaldehyde, methylmercuric hydroxide, urea or formamide are incorporated into the gel matrix. In spite of the high resolution achieved analytically, extraction of biologically active mRNA on a preparative scale from discrete gel bands proved to be rather difficult".

The method proposed by Graeve et al. is HPLC gel filtration and the results are described by the authors on page 1564 as follows:
"The preparative separation of relatively small RNAs such as globin mRNA or snRNAs appears to be particularly attractive. Resolution of high molecular weight RNAs is less satisfactory, because one has to work under nondenaturing conditions".

It is thus, seen that while there has been a long-felt need for the preparative recovery of mRNA fractions, no satisfactory method for this purpose has so far been reported. It is particularly noteworthy that in spite of such long-felt need, it never occurred to one in the scientific community to try and remove resolved mRNA fraction from an electrophoresis matrix by the reversible linkage to poly-U or poly-dT carrier sheets via H-bridges.

In accordance with the present invention, it has now surprisingly been found that the for the successful removal of mRNA fractions from an electrophoresis matrix, it is not necessary to apply irreversible covalent or strong polar bonds, and that it is also possible to apply reversible hydrogen bridge bonds such as occur upon interaction between mRNA and poly-U or poly-dT.

The present invention provides in one of its aspects a method for the preparative recovery of electrophoretically resolved mRNA fractions from the matrix of the electrophoretic resolution, comprising applying to the matrix a carrier sheet of derivative cellulose or nitrocellulose bearing a plurality of residues selected from the group of polyuridylic acid and polythymidylic acid resideus, cutting said carrier sheet into strips each of which holds an mRNA fraction and eluting an mRNA fraction from any desired strip.

Thus, in accordance with the invention there is provided a simple and effective method for the preparation of pure mRNA free of the difficulties which are inherent in known methods by which mRNA is eluted in a complex set of operations from the electrophoresis matrix itself.

The invention also provides a process for the preparative recovery of a mRNA fraction from cell material comprising extracting total RNA from the cell material by methods known per se, separating a mixture of mRNA fractions from all other RNA by means of column chromatography on derivative powderous cellulose or powderous agarose bearing a plurality of residues selected from the group of polyuridylic acid (poly-U) and poly-thymidylic acid (poly-dT) residues, isolating a total mRNA fraction, subjecting the so-isolated total mRNA fraction to electrophoresis, transferring the resolved mRNA fractions from the electrophoresis matrix to a carrier sheet of derivative cellulose or nitrocellulose bearing a plurality of residues selected from the group of poly-U and poly-dT residues, cutting said carrier sheet into strips each holding an mRNA fraction and eluting an mRNA fraction from any desired strip.

By yet another aspect, the invention provides for use in the above methods a sheet of derivative cellulose or nitrocellulose comprising a plurality of residues selected from the group of poly-U and poly-dT residues.

The invention is illustrated in the following examples without being limited thereto:

EXAMPLE 1

Preparation of poly-U or poly-dT paper (a) Binding to Paper

Poly-U may be covalently bound to a variety of derivatized paper supports, e.g., diazo-benzyloxymethyl paper (DBM) (Alwine et al. 1977) and/or diazothiophenyl paper (DTP) (Brian Seed unpublished observations). Both the DBM and DTP papers are hereafter referred to a activated paper. The activated paper immediately following its diazotization is washed extensively in 50 mM sodium acetate buffer pH 5.5. Prior to its binding to the activated paper, any contaminating small amine molecules (e.g. trishydroxylaminomethane) are removed from the poly-U solution. Ten millilitres (ml) of the poly-U solution at a final concentration of 2 mg/ml in 50 mM sodium acetate pH 5.5 buffer is added directly to a $20 \times 15$ cm sheet of the activated paper. The sheet is then sealed in a plastic bag and incubated at 40° C. for 48 hours. This stage is referred to as "binding". Binding of poly-dT is performed in a completely analogous manner.

(b) Wash of Poly-U or Poly-dT paper

In order to inactivate any excess diazonium groups and to saturate non-specific binding sites for nucleic acids, the poly-U (or poly-dT) paper is washed for 5 minutes in 50 ml of wash buffer which contains the following: 50 mM Nacl, 100 mM Tris-HCL pH 7.6, 1% glycine, 0.02% polyvinylpyrillidone (Sigma, average M.W. 360,000) 0.2% Ficoll (Pharmacia, average M.W. 400,000 daltons) and 100 microgram ($\mu$g)/ml commercially available transfer RNA. The poly-U (or poly-dT) paper is then incubated at 40° C. with 4 changes of the above wash buffer (50 ml each wash) for 24 hours. The poly-U (or poly-dT) paper is washed twice (60 minutes each wash) at 20° C. with 500 ml of 500 mM NaCl, 10 mM Tris-HCL ph 7.6 followed by washing twice for 60 minutes with 500 ml of distilled water at 20° C. and then incubated in boiling distilled water for 3 minutes, washed twice for 10 minutes in 50 ml distilled water at 20° C. and then dried and stored at −20° C.

EXAMPLE 2

Preparation of Poly-U nitrocellulose or Poly-dT nitrocellulose

Poly-U is dissolved in 3M NaCl, 0.3 M sodium citrate pH 7.0 to a final concentration of 2 mg/ml and the solution is added direction to a dry nitrocellulose sheet that had been pretreated with H$_2$O, equilibrated with 3M NaCl, 0.3 M sodium citrate pH 7.0 and dried under a lamp. The sheet is then air dried and baked in an oven set at 80° C. for 2 hours. The poly-U nitrocellulose is then processed exactly as described in part(b) of Example 1.

Poly-dT nitrocellulose is prepared in the same manner.

EXAMPLE 3

Isolation of mRNA from Gels mRNA molecules are first resolved electrophoretically in either agarose or acrylamide gels. Any one of a number of suitable published methods may be employed for the electrophoretic separation, under denaturing conditions, of the mRNA. These may include using denaturants such as 7M urea (Smith and Furnichi, 1980, Donis-Keller et al., 1977), 2.2M formaldehyde (Lehrach et al., 1977) and 10 mM methylmercury gels (Lehrach et al., 1977). Use of 7M urea as denaturant is the preferred technique. Following electrophoresis, the gel is equilibrated in 500 mM NaCl, 10 mM Tris-Acetate pH 7.6 by rocking the gel with four 500 ml changes of this buffer at room temperature for 2 hours. The resolved mRNA molecules in the gel are then transferred to a carrier sheet of poly-U paper, poly-dT paper, poly-U nitrocellulose or poly-dT nitrocellulose, by any one of a number of currently available published transfer technqiues including blotting (Southern, 1975 loc. cit), vacuum blotting (PeFeroen, 1982 loc. cit) and electrotransfer (Bittner et al., 1980 loc. cit). This transfer takes place with the gel in direct contact with the poly-U paper and the transfer solution must be of sufficiently high ionic concentration to allow for the formation of hydrogen bonds between the poly A+ mRNA and the carrier sheet. A transfer solution of 500 mM NaCl, 10 mM Tris-Acetate pH 7.6 works well. Following the transfer, the carrier sheet with the resolved mRNA molecules bound, is washed in 500 mM NaCl, 10 mM Tris-acetate pH 7.6, and the cut into small (1–2 mm width) horizontal segments. Each segment of poly-U paper is placed in a test-tube and washed with distilled water at room temperature (20° C.). With poly-U paper and/or poly-U nitrocellulose this procedure will elute little or not mRNA. The poly-U paper segment is then incubated at 70° C. for 3 minutes with a small volume of distilled water. This simple procedure (a 3-minute incubation) readily elutes free of contaminating substances all bound mRNA molecules into pure, distilled water.

What is claimed is:

1. A method for the preparative recovery of mRNA from a RNA-containing cell mateial, said method comprising the steps of:
    (a) extracting RNA from a cell;
    (b) resolving said RNA into a plurality of RNA fractions, at least one of said RNA fractions including mRNA;
    (c) separating said mRNA from said RNA;
    (d) resolving said mRNA into a plurality of mRNA fractions;
    (e) contacting a carrier sheet bearing at least one acid residue capable of hydrogen-bonding with at least one of said mRNA fractions, said carrier sheet being formed of a material selected from the group consisting of a cellulose derivative, a nitrocellulose derivative, and a mixture of cellulose derivative and a nitrocellulose derivative; wherein said carrier sheet is coated with an acid selected from the group consisting of polyuridylic acid, polythymidylic acid, and a mixture of polyuridylic acid and polythymidylic acid;

(f) cutting said carrier sheet into a strip including said one of said at least one of said mRNA fractions adhered to said carrier sheet; and (g) eluting said one of said at least one of said mRNA fractions adhered to said strip of said carrier sheet.

2. The method as defined by claim 1, comprising, in step (c), separating said mRNA from said RNA by column chromatography.

3. The method as defined by claim 1, comprising, in step (c), separating said mRNA from said RNA by column chromatography on a substrate bearing a plurality of acid residues selected from the group consisting of polyuridylic acid, polythymidylic acid, and a mixture of polyuridylic acid and polythmidylic acid.

4. The method as defined by claim 3, wherein said substrate comprises a material selected from the group consisting of a powdered cellulose derivative, a powdered agarose derivative, and a mixture of powdered cellulose derivative and powdered agarose derivative.

5. The method as defined by claim 1, comprising, in step (d), resolving said mRNA by electrophoresis on a gel matrix.

6. The method as defined by claim 5, comprising, in step (e), contacting said carrier sheet with at least one of said mRNA fractions after said mRNA is resolved by electrophoresis on said gel matrix.

7. A method for preparatively separating mRNA from a RNA-containing cell material, said method comprising the steps of:

(a) extracting RNA from a cell;

(b) resolving said RNA into a plurality of RNA fractions, at least one of said RNA fractions including mRNA; and (c) contacting a carrier sheet with said mRNA to hydrogne-bond said mRNA onto said carrier sheet, said carrier sheet being formed of a material selected from the group selected from the group consisting of a cellulose derivative, a nitrocellulose derivative, and a mixture of cellulose derivative and a nitrocellulose derivative; wherein said carrier sheet is coated with an acid selected from the group consisting of polyuridylic acid, polythmidylic acid, and a mixture of polyuridylic acid and polythymidylic acid.

8. The method as defined by claim 7, comprising resolving said mRNA into a plurality of mRNA fractions by electrophoresis on a gel maxtrix.

9. The method as defined by claim 8, comprising, in step (c), contacting said carrier sheet with said gel matrix.

10. The method as defined by claim 9, further comprising, after step (c);

(d) cutting off at least one portion of said carrier sheet containing at least one of said mRNA fractions.

11. The method as defined by claim 10, further comprising, after step (d);

(e) eluting said at least one of said mRNA fractions from said at least one portion of said carrier sheet.

12. The method as defined by claim 7, wherein said carrier sheet comprises a cellulose derivative.

13. The method as defined by claim 7, wherein said carrier sheet comprises a nitrocellulose derivative.

14. The method as defined by claim 12, wherein said carrier sheet is coated with a polyuridylic acid residue.

15. The method as defined by claim 12, wherein said carrier sheet is coated with a polythymidylic acid residue.

16. The method as defined by claim 12, wherein said carrier sheet is coated with a mixture of polyuridylic acid and polythymidylic acid residues.

17. The method as defined by claim 13, wherein said carrier sheet is coated with a polyuridylic acid residue.

18. The method as defined by claim 13, wherein said carrier sheet is coated with a polythymidylic acid residue.

19. The method as defined by claim 13, wherein said carrier sheet is coated with a mixture of polyuridylic acid and polythymidylic acid residues.

20. The method as defined by claim 1 wherein said material is a cellulose derivative.

21. The methods as defined by claim 1 wherein said material is a nitrocellulose derivative.

22. The method as defined by claim 1 wherein said material is a mixture of cellulose derivative and nitrocellulose derivative.

23. The method as defined by claim 1 wherein said acid is polyuridylic acid.

24. The method as defined by claim 1 wherein said acid is polythymidylic acid.

25. The method as defined by claim 1 wherein said acid is a mixture of polyuridylic acid and polythymidylic acid.

26. A carrier sheet adapted for use in the preparative recovery of mRNA from a RNA-containing cell material, said carrier sheet being formed of a mterial selected from the group consisting of a cellulose derivative, a nitrocellulose derivative and a mixture of cellulose derivative and nitrocellulose derivative; wherein said carrier sheet is coated with an acid selected from the group consisting of polyuridylic acid, polythymidylic acid and a mixture of polyuridylic acid and polythymidylic acid.

27. The carrier sheet as defined by claim 26 wherein said material is a cellulose derivative.

28. The carrier sheet as defined by claim 26 wherein said material is a nitrocellulose derivative.

29. The carrier sheet as defined by claim 26 wherein said material is a mixture of cellulose derivative and nitrocellulose derivative.

30. The carrier sheet as defined by claim 26 wherein said acid is polyuridylic acid.

31. The carrier sheet as defined by claim 26 wherein said acid is polythymidylic acid.

32. The carrier sheet as defined by claim 26 wherein said acid is a mixture of polyuridylic acid and polythymidylic acid.

* * * * *